United States Patent
Brooks

(10) Patent No.: US 11,389,380 B2
(45) Date of Patent: Jul. 19, 2022

(54) DEODORANT COMPRISING A ZINC CARBOXYLATE SALT AND ALUMINUM CHLOROHYDRATE

(71) Applicant: GIVAUDAN SA, Vernier (CH)

(72) Inventor: Matthew Peter Brooks, Ashford (GB)

(73) Assignee: GIVAUDAN SA, Vernier (CH)

( * ) Notice: Subject to any disclaimer, the term of this patent is extended or adjusted under 35 U.S.C. 154(b) by 550 days.

(21) Appl. No.: 16/341,780

(22) PCT Filed: Nov. 8, 2017

(86) PCT No.: PCT/EP2017/078605
§ 371 (c)(1),
(2) Date: Apr. 12, 2019

(87) PCT Pub. No.: WO2018/087148
PCT Pub. Date: May 17, 2018

(65) Prior Publication Data
US 2021/0369575 A1    Dec. 2, 2021

(30) Foreign Application Priority Data

Nov. 10, 2016 (GB) .................................. 1619015
Jun. 6, 2017 (GB) .................................. 1708986

(51) Int. Cl.
| | |
|---|---|
| *A61K 8/27* | (2006.01) |
| *A61K 8/04* | (2006.01) |
| *A61K 8/26* | (2006.01) |
| *A61K 8/34* | (2006.01) |
| *A61Q 15/00* | (2006.01) |

(52) U.S. Cl.
CPC ................ *A61K 8/27* (2013.01); *A61K 8/046* (2013.01); *A61K 8/26* (2013.01); *A61K 8/34* (2013.01); *A61Q 15/00* (2013.01)

(58) Field of Classification Search
CPC ............. A61K 8/26; A61K 8/27; A61K 8/361
See application file for complete search history.

(56) References Cited

U.S. PATENT DOCUMENTS

| | | | |
|---|---|---|---|
| 4,518,582 A | 5/1985 | Schamper | |
| 2,087,161 A1 | 7/2003 | Hudson | |
| 2005/0163737 A1 | 7/2005 | Lemoine et al. | |
| 2005/0180935 A1 | 8/2005 | Lemoine et al. | |
| 2010/0068160 A1 | 3/2010 | Springer et al. | |
| 2014/0242198 A1 * | 8/2014 | Modak .................. | A01N 59/00 424/736 |
| 2015/0283044 A1 | 10/2015 | Swaile et al. | |

FOREIGN PATENT DOCUMENTS

| | | | | |
|---|---|---|---|---|
| EP | 1541122 A1 | 11/2004 | | |
| EP | 1541123 A1 | 6/2005 | | |
| EP | 1563829 A1 * | 8/2005 | ............. | A61Q 15/00 |
| EP | 1563829 A1 | 8/2005 | | |
| EP | 1714638 A1 | 3/2006 | | |
| EP | 1714638 A1 * | 10/2006 | ............... | A61K 8/26 |
| GB | 996560 | 6/1962 | | |
| RU | 2007106055 A | 8/2008 | | |
| WO | 0199376 A2 | 12/2001 | | |
| WO | WO-0199376 A2 * | 12/2001 | ............. | A61K 8/496 |
| WO | 2005009404 A1 | 2/2005 | | |
| WO | 2006007989 A1 | 1/2006 | | |
| WO | 2007003635 A1 | 1/2007 | | |
| WO | 2014095366 A3 | 6/2014 | | |
| WO | 2014095475 A1 | 6/2014 | | |
| WO | WO-2014095475 A1 * | 6/2014 | ............... | A61K 8/26 |
| WO | 2015022315 A2 | 2/2015 | | |

OTHER PUBLICATIONS

EP-1563829-A1 (Espacenet English translation, downloaded Nov. 2021) (Year: 2021).*
WO-0199376-A2 (Espacenet English translation, downloaded Nov. 2021) (Year: 2021).*
WO-2014095475-A1 (WIPO English translation, downloaded 2021) (Year: 2021).*
EP-1714638-A1 (Espacenet English translation, downloaded 2021) (Year: 2021).*
International Search Report and Written Opinion of the International Searching Authority for corresponding application PCT/EP2017/078605 dated Dec. 13, 2017.
GB Search Report for corresponding application GB 1708986.3 dated Feb. 26, 2018.

\* cited by examiner

*Primary Examiner* — Mark V Stevens
(74) *Attorney, Agent, or Firm* — Norris McLaughlin PA

(57) ABSTRACT

An advantageous deodorizing composition comprising at least one zinc carboxylate salt and aluminium chlorohydrate is provided, as well as a deodorant consumer product comprising the same. Furthermore, a method of suspending aluminium chlorohydrate in an at least essentially anhydrous solvent is provided, as well as a method of preventing clumping of aluminium chlorohydrate in a deodorizing composition or a deodorant consumer product and a method of preventing clogging of a nozzle of a deodorant spray containing a deodorizing composition.

24 Claims, 1 Drawing Sheet

DEODORANT COMPRISING A ZINC CARBOXYLATE SALT AND ALUMINUM CHLOROHYDRATE

This is an application filed under 35 USC 371 based on PCT/EP2017/078605, file on 8 Nov. 2017, which in turn is based on GB 1619015.9 filed 10 Nov. 2016, and GB 1708986.3 filed 6 Jun. 2017. The present application claims the full priority benefit of these prior applications and herein incorporates by reference the full disclosures of these prior applications.

FIELD OF THE INVENTION

This disclosure is concerned with deodorizing compositions useful in preventing or suppressing human, animal and environmental malodour, and in particular human body malodour.

BACKGROUND OF THE INVENTION

Deodorant active agents are ingredients, or formulations, that are designed either to mask malodours once they are formed, or to prevent or hinder their formation.

Masking of malodours involves the use of fragrance ingredients, acting in the gaseous phase to create an olfactory signal that reduces a human subject's perception of any malodour present.

Malodour prevention or suppression employs deodorant active agents to eliminate malodorous substances either directly reacting or interacting with them chemically, or by deactivating or interrupting the pathways by which malodorous substances are formed. Taking human body malodour as an example, the latter method either involves the use of bactericides or bacteriostatic agents to disrupt local populations of micro-organisms that act on malodour precursor compounds contained in sweat to generate malodours, and/or it involves the use of ingredients, such as astringent anti-perspirant ingredients (typically aluminium or zirconium salts) to prevent or reduce the flux of sweat.

The principal disadvantage of many deodorant or antiperspirant active ingredients is that some of the commonly employed ingredients, such as the aforementioned aluminium or zirconium salts or bactericides and bacteriostatic agents, are perceived as being unfriendly to human skin, or to populations of micro-flora contained on human skin. Consequently, there is a desire in the industry to reduce or even eliminate the use of these materials. This is particularly the case with regard to their use in cosmetic products intended to be applied topically on human skin.

Aluminium salts used in deodorants perform two key functions: reducing perspiration (sweating) and reducing the development of body odour. The levels of aluminium salts vary by applicator type:

Sticks and oil gels: typically >15% and often >20%
Roll-ons: typically >5% and often >10%
Aerosols: typically <10%

Aluminium chlorohydrate (ACH) is an antiperspirant active that is commonly used to address underarm sweating and malodour formation. The solid aluminium chlorohydrate is suspended into aerosol formulations that must be anhydrous. This is due to aluminium chlorohydrate clumping when water is present, which will prevent the aluminium chlorohydrate from being actuated and potentially cause the nozzle to become blocked.

Furthermore, incorporation of aluminium chlorohydrate into deodorant formulations gives rise to an acidic formulation (typically about pH2-3). This is much lower than skin pH, which can cause discomfort and/or reddening in the underarm. Additionally, lowering skin pH will influence underarm malodour since carboxylic acids are a major component of the odour and decreasing pH shifts the equilibrium to the protonated (volatile) form.

Whilst aluminium salts are highly effective actives, they have also some drawbacks in terms of staining and marking of clothing. In an attempt to reduce or eliminate these visible signs of aluminium salts, in particular the yellow staining of t-shirts and vests that are directly in contact with the underarm, the amount incorporated into the consumer product is sometimes reduced below the level that provides optimal odour protection ("no white mark products"). In such a situation, additional odour protection is advantageous.

Zinc carboxylates represent a genus of deodorant active ingredients, generally recognized as safe, that act to exert a malodour-counteracting or eliminating effect by interacting or reacting chemically with malodorous ingredients, such as the myriad sulphur- or nitrogen-containing ingredients, or short-chain fatty acids, found in sweat. Zinc ricinoleate is a particular example of a zinc carboxylate that is often mentioned in the prior art in the context of deodorant applications.

Substantially all deodorant compositions will combine both odour-masking ingredients (fragrances) and odour-preventing/suppressing active ingredients. A challenge for formulators, therefore, is to ensure that the odour-preventing/suppressing active ingredients and the odour masking ingredients do not interfere with each other, but rather complement each other in order that the overall odour-prevention/suppression/masking attributes of these ingredients, as well as the hedonic effects, are exploited to the full.

For example, whilst fragrance ingredients can play an important odour-masking role in deodorant compositions, they are also employed in deodorant compositions with aesthetic considerations in mind, and the use of a deodorant active ingredient should not cause or contribute to deodorant compositions having an unbalanced, unappealing or even unpleasant scent impression.

On the other hand, deodorant active ingredients, such as the zinc carboxylates, that interact chemically to absorb malodorous compounds are generally regarded to lack efficacy unless their incorporation levels in deodorant compositions are sufficiently high. In order to exert an acceptable odour-preventing/suppressing effect, these active ingredients need to be easily incorporated into fragrance-containing deodorant composition bases, and preferably be readily soluble or miscible therein at efficacious levels.

However, it is a particular disadvantage with the malodour-counteracting zinc carboxylates that they are not easily incorporated into fragrance-containing deodorant compositions. In particular, residual free acids contained in lower molecular weight homologue zinc carboxylates tend to be foul-smelling and can disturb and unbalance the scent impression of any deodorant composition containing them. On the other hand, higher molecular weight homologue zinc carboxylates, such as zinc ricinoleate, owing to the relatively low levels of zinc ions for a given mass of zinc carboxylate and are consequently difficult to load at sufficiently high levels in deodorant bases to impart an acceptable deodorancy effect. Their lack of efficacy can be further exacerbated by their poor solubility in deodorant bases. Furthermore, poor solubility impact on their deodorizing efficacy, the insoluble material when administered to a site in need of treatment, can leave unsightly residues. Still further, when deodorant compositions are in aerosol format, un-dissolved material can cause nozzle clogging.

There remains a need to provide deodorant active ingredients and deodorant compositions containing same that can deliver high levels of perceived malodour-reduction when applied to a site containing a malodorous source. There is a particular need for deodorant active ingredients and deodorant compositions containing same that can deliver high levels of perceived malodour-reduction when applied topically to a human subject, and particularly the under arm area of a human subject. There is, moreover, a need to provide deodorant actives that can be easily incorporated at efficacious levels into fragrance-containing deodorant compositions, and which do not cause or contribute to an unbalanced, unappealing or even an unpleasant overall scent impression.

Furthermore, in the context of deodorant compositions comprising aluminium chlorohydrate, there is a need to prevent aluminium chlorohydrate from clumping when water is present, to avoid discomfort and/or reddening in the underarm, and to eliminate the drawbacks in terms of staining and marking of clothing while, at the same time, providing sufficient odour protection.

SUMMARY OF THE INVENTION

Figure 1:
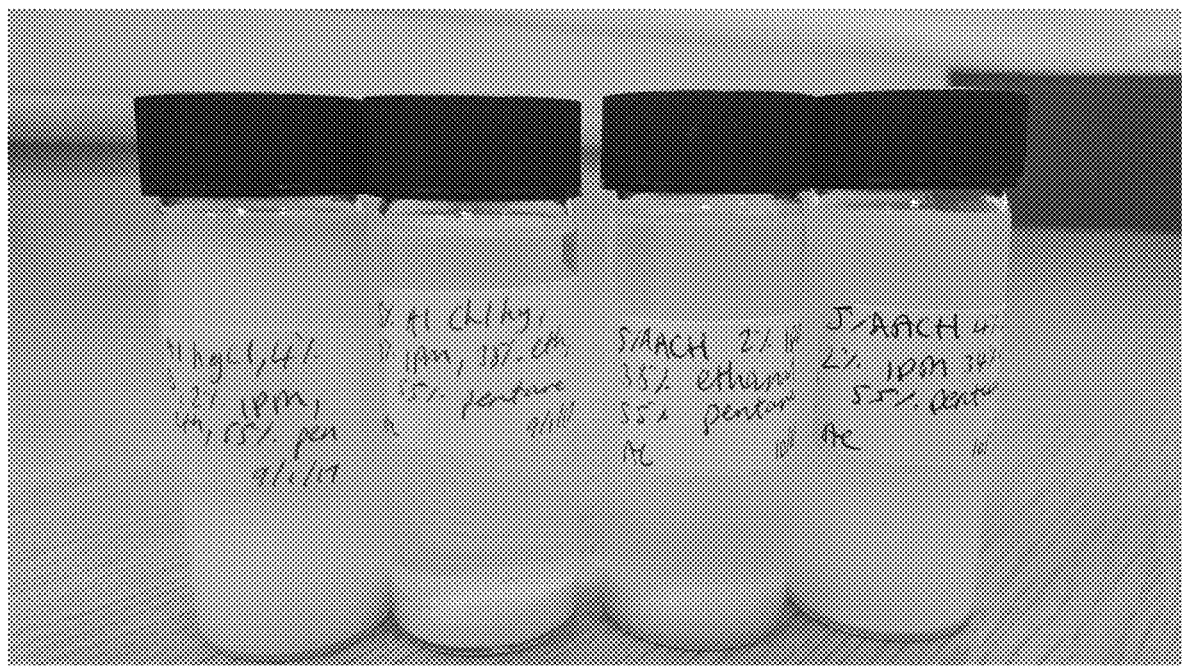
FIG. 1 is a photograph of glass vials containing tested compositions, including glass vials containing both aluminum chlorohydrate and zinc neodecanoate.

It was discovered that the performance of deodorant compositions, and in particular fragrance-containing deodorant compositions useful in the control of human, animal and environmental malodours, but particularly human body odour, can be improved by the addition to said composition of a deodorizing agent containing at least one zinc carboxylate salt, in particular zinc neodecanoate.

Alternatively or in addition to the at least one zinc carboxylate salt, it would also be possible to include any other zinc salt that is a liquid. In particular, said other zinc salt should be liquid at ambient temperature (20-25° C.) and a pressure from atmospheric pressure to aerosol canister pressure (0.7-9.8 bar).

More particularly, it was found that zinc carboxylate salts, especially zinc neodecanoate, can be incorporated into deodorant composition bases in a surprisingly facile manner. Furthermore, such deodorant compositions applied to a site of a source of malodour can deliver a deodorancy benefit and a sustained, undistorted and pleasant scent impression.

The use of zinc neodecanoate in deodorant compositions has been previously described in GB patent application No. 1619015.9, the disclosure of which is herewith incorporated by reference.

Surprisingly, it was now found that aluminium chlorohydrate remains suspended in alcoholic aerosol formulations that contain at least one zinc carboxylate salt, especially zinc neodecanoate. This allows the aluminium chlorohydrate remain available for delivering anti-perspirant and malodour performance benefits in non-anhydrous formulations. This beneficial effect of the zinc carboxylate salt is true for both standard and 'activated' forms of aluminium chlorohydrate. Furthermore, thanks to the improved suspension of the aluminium chlorohydrate in the aerosol formulation, vigorous shaking prior to use is no longer indispensable. In particular, only mild shaking or even no shaking is necessary prior to product application.

Zinc neodecanoate was also found to be highly effective at controlling axillary odour. In particular, it was shown that combining zinc neodecanoate with aluminium salts provides no white marks without compromising malodour performance:
  inclusion of low levels of aluminium salts provides some reduction in perspiration without causing the unsightly staining or marking of clothes
  inclusion of zinc neodecanoate provides additional odour control The use of zinc neodecanoate or other zinc carboxylate salts in underarm deodorant products therefore allows for the partial or complete removal of aluminium salts from the formulation.

The effect of reducing or eliminating the highly acidic buffering effect of aluminium salts is two-fold:
  Following application of the deodorant products, the underarm pH is closer to that of 'natural' skin pH (circa 5.5)
  The headspace concentration of acidic malodorants is greatly reduced (compared to when high levels of aluminium chlorohydrate are present)

Surprisingly, it was further found that inclusion of zinc neodecanoate in deodorant products does not produce the same yellow staining of fabrics after repeated wearing and washing, whilst still delivering malodour performance.

In a first aspect, the present invention therefore provides a deodorizing composition comprising at least one zinc carboxylate salt, in particular zinc neodecanoate, and aluminium chlorohydrate.

In a second aspect, the present invention provides a deodorant consumer product comprising the deodorizing composition of the present invention.

In a third aspect, the present invention provides a method of suspending aluminium chlorohydrate in an at least essentially anhydrous solvent, wherein at least one zinc carboxylate salt is added.

In a fourth aspect, the present invention provides a method of preventing clumping of aluminium chlorohydrate in a deodorizing composition or a deodorant consumer product, wherein the deodorizing composition or deodorant consumer product is provided with at least one zinc carboxylate salt.

In a fifth aspect, the present invention provides a method of preventing clogging of a nozzle of a deodorant spray containing a deodorizing composition, said a deodorizing composition comprising aluminium chlorohydrate, wherein the deodorizing composition is provided with at least one zinc carboxylate salt.

In a sixth aspect, the present invention relates to the use of at least one zinc carboxylate salt, in particular zinc neodecanoate, in combination with aluminium chlorohydrate in a deodorizing composition. In particular, said combination of at least one zinc carboxylate salt and aluminium chlorohydrate may be used as a deodorizing agent for preventing or suppressing human, animal and environmental malodour, and especially human body malodour.

These and other aspects of the invention will be further understood in view of the following detailed description of particular embodiments of the invention.

DETAILED DESCRIPTION OF THE INVENTION

The deodorizing composition of the present invention comprises at least one zinc carboxylate salt and aluminium chlorohydrate. By combining these active ingredients, the desired level of odour protection can be achieved while avoiding the drawbacks of aluminium chlorohydrate.

Preferably, the at least one zinc carboxylate salt is selected from the group consisting of zinc neodecanoate, zinc ricinoleate, and zinc acetate. More preferably, it is or at least comprises zinc neodecanoate.

In particular, clumping of the deodorizing composition, and thereby blocking of a nozzle in the case of use as an aerosol, is avoided, even if small or even moderate levels of water are present, e.g. from a solvent. This allows for the use of solvents that may contain small amounts of water, such as ethanol, for instance. In particular, such a solvent may contain up to 5% by weight of water.

Furthermore, the pH of the deodorizing composition of the present invention is higher than that of known compositions comprising only aluminium chlorohydrate but no zinc carboxylate salt, especially no zinc neodecanoate. Thanks to this, irritation of the skin in the area of use of the deodorizing composition is significantly reduced, e.g. in the underarm, thereby avoiding discomfort and/or reddening.

A further advantage of the deodorizing composition of the present invention is that also staining and marking of clothing prevented, even if aluminium chlorohydrate is present in levels higher than those typically used in "no white mark products".

Apart from this, zinc carboxylate salts, and especially zinc neodecanoate, are easily incorporated into fragrance-containing deodorant compositions. Zinc neodecanoate in neat form is a pourable liquid and can be used as the deodorizing agent, as such.

Interestingly, when combined with glutamine derivative (1), the effect of the two ingredients is perfectly additive, and enhanced effects are seen when combining the two ingredients.

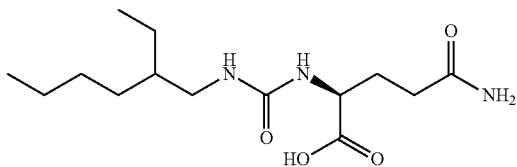

(I)

Glutamine derivative (I) has been previously described in WO 2012/056014 as a broadly AMRE-active compound inhibiting malodour formation from axilla bacteria. The disclosure of WO 2012/056014 in this respect is herewith incorporated by reference.

Both the at least one zinc carboxylate salt and aluminium chlorohydrate should be provided in the deodorizing composition in effective amounts. Preferably, zinc neodecanoate is used.

In a preferred embodiment, the deodorizing composition of the present invention comprises the at least one zinc carboxylate salt, and especially zinc neodecanoate, in a concentration of from about 1% by weight to about 100% by weight, more preferably from about 1% by weight to about 20% by weight, and most preferably from about 2% by weight to about 8% by weight. Particularly preferred is a concentration of zinc neodecanoate of about 4% by weight.

The deodorizing composition of the present invention typically comprises the at least one zinc carboxylate salt, especially zinc neodecanoate, and aluminium chlorohydrate in a weight ratio of from about 20:1 to about 1:20, more preferably in a weight ratio of from about 10:1 to about 1:10.

In a preferred embodiment, the deodorizing composition of the present invention comprises the at least one zinc carboxylate salt, especially zinc neodecanoate, and aluminium chlorohydrate in a weight ratio of from about 2:1 to about 1:10, more preferably in a weight ratio of from about 1.5:1 to about 1:5, and most preferably in a weight ratio of from about 1:1 to about 1:2. Particularly preferred is a weight ratio of about 4:5.

In a particularly preferred embodiment, the deodorizing composition of the present invention comprises zinc neodecanoate in a concentration of 4% by weight and aluminium chlorohydrate in a concentration of 5% by weight.

Zinc neodecanoate is commercially available and can be prepared according to well-known procedures. Preferably, zinc neodecanoate is prepared from purified neodecanoic acid. Suitable methods for purifying neodecanoic acid are described in examples 3 and 4 below, for instance.

Preferably, the deodorizing composition of the present invention further comprises a suitable solvent, such as isopropyl myristate. Solvents typically used in deodorizing compositions are well-known in the art and depend, to a certain extent, on the intended use and in particular the type of consumer product.

As has been described above, the unique combination of active ingredients in the deodorizing composition of the present invention allows for the presence of small amounts of water in the composition without the drawbacks generally known for compositions comprising aluminium chlorohydrate. Nevertheless, the composition preferably comprises an at least essentially anhydrous solvent.

An "at least essentially anhydrous solvent", as used throughout this application, refers to a solvent containing less than 5% by weight of free water; "free water" being water other than the water of hydration associated with any particular component. Preferably, anhydrous solvents have less than 2% by weight free water, more preferably less than 1% and most preferably less than 0.5%.

Suitable solvents include, but are not limited to, ethanol, cyclomethicone, and glycol ether, such as dipropylene glycol methyl ether (e.g. Dowanol™ DPM from Dow Chemical) or tripropylene glycol methyl ether (Dowanol™ TPM from Dow Chemical). Preferred solvents are ethanol or cyclomethicone.

In a preferred embodiment, the deodorizing composition of the present invention further comprises at least one fragrance ingredient, preferably at least five, more preferably at least 10, and most preferably at least 20 fragrance ingredients, but may also be much higher.

Any fragrance ingredients may be employed in the fragrance component. Non-limiting examples of fragrance ingredients suitable for use are described in standard reference works used in the perfumery industry, for example in Arctander, Perfume and Flavour Chemicals (Aroma Chemicals), vol. I and II (1969), and any later volumes and editions of that work.

In a particular embodiment of the invention, the deodorizing composition may contain at least one fragrance ingredient that is particularly efficient at exerting a malodour counteracting effect. Malodour-counteracting fragrance ingredients are known in the art. However, we have found certain fragrance ingredients that are particularly effective malodour-counteracting ingredients when used alone or in combination.

Therefore, in a preferred embodiment, the deodorizing composition of the present invention further comprises at least one fragrance ingredient selected from the group consisting of 3,7-dimethyloct-6-enal, e.g. Citronellal; 3,7-dimethyloct-6-en-1-ol, e.g. Citronellol; 2,4-dimethylcyclohex-3-enecarbaldehyde, e.g. Cyclal C; (E)-dec-4-enal; ethyl 2-methyl butyrate; 1-phenylethyl acetate, e.g. Gardenol; (Z)-hex-3-en-1-yl acetate; hexyl acetate; isoamyl acetate; *Litsea cubeba* oil; Nonanal; Orange oil; Orange terpenes; prenyl acetate; 4-methyl-2-(2-methylprop-1-en-1-yl)tetrahydro-2H-pyran, e.g. Rose Oxide; 4-methylene-2-phenyltetrahydro-2H-pyran, e.g. Rosyrane super; 2,4-dimethylcyclohex-3-enecarbaldehyde; e.g. Tricyclal; 2,6,10-trimethylundec-9-enal, e.g. Adoxal; Armoise oil Morocco; 8-(sec-butyl)-5,6,7,8-tetrahydroquinoline, e.g. Bigaryl; (2E)-3-phenylprop-2-enal, e.g. Cinnamic aldehyde; (E)-3,7-dimethylocta-2,6-dienal, e.g. Citral; ethyl caproate; 1,3,3-trimethyl-2-oxabicyclo[2.2.2]octane, e.g. Eucalyptol; *Eucalyptus*, e.g. *globulus* oil China; 1-(1,2,8,8-tetramethyl-1,2,3,4,5,6,7,8-octahydronaphthalen-2-yl)ethanone, e.g. Georgywood; hexyl isobutyrate; (E)-4-(2,6,6-trimethylcyclohex-1-en-1-yl)but-3-en-2-one, e.g. Ionone beta; isobutyl isobutyrate; isobutyl quinolone; isopropyl methyl-2-butyrate; (2E,6Z)-3,7-dimethylnona-2,6-dienenitrile, e.g. Lemonile; 3,7-dimethylocta-1,6-dien-3-ol, e.g. Linalool; 2,6-dimethylhept-5-enal, e.g. Melonal; methyl amyl ketone; methyl benzoate; methyl heptenone; methyl hexyl ketone; phenyl ethyl acetate; tetrahydro myrcenol; Patchouli Oil; tridecen-2-nitrile; 6-methoxy-2,6-dimethyloctanal, e.g. Calypsone; 5-tert-butyl-2-methyl-5-propyl-2H-furan, e.g. Cassyrane; (4E)-9-hydroxy-5,9-dimethyl-4-decenal, e.g. Mahonial; 1-methyl-2-(5-methylhex-4-en-2-yl)cyclopropyl) methanol, e.g. Rosyfolia; 3-(4-isobutyl-2-methylphenyl) propanal, e.g. Nympheal; and mixtures thereof.

In a more particular embodiment, the fragrance component may be provided such that it contains at least 2, at least 3, at least 4, at least 5 of the following ingredients: 3,7-dimethyloct-6-enal, e.g. Citronellal; 3,7-dimethyloct-6-en-1-ol, e.g. Citronellol; 2,4-dimethylcyclohex-3-enecarbaldehyde, e.g. Cyclal C; (E)-dec-4-enal; Ethyl 2-methyl butyrate; 1-phenylethyl acetate, e.g. Gardenol; (Z)-hex-3-en-1-yl acetate; Hexyl acetate; isoamyl acetate; *Litsea cubeba* oil; Nonanal; Orange oil; Orange terpenes; prenyl acetate; 4-methyl-2-(2-methylprop-1-en-1-yl)tetrahydro-2H-pyran, e.g. Rose Oxide; 4-methylene-2-phenyltetrahydro-2H-pyran, e.g. Rosyrane super; 2,4-dimethylcyclohex-3-enecarbaldehyde; e.g. Tricyclal; and optionally at least 2, at least 3, at least 4, at least 5 of the following ingredients: 2,6,10-trimethylundec-9-enal, e.g. Adoxal; Armoise oil Morocco; 8-(sec-butyl)-5,6,7,8-tetrahydroquinoline, e.g. Bigaryl; (2E)-3-phenylprop-2-enal, e.g. Cinnamic aldehyde; (E)-3,7-dimethylocta-2,6-dienal, e.g. Citral; Ethyl caproate; 1,3,3-trimethyl-2-oxabicyclo[2.2.2] octane, e.g. Eucalyptol; *Eucalyptus*, e.g. *globulus* oil China; 1-(1,2,8,8-tetramethyl-1,2,3,4,5,6,7,8-octahydronaphthalen-2-yl)ethanone, e.g. Georgywood; Hexyl isobutyrate; (E)-4-(2,6,6-trimethylcyclohex-1-en-1-yl)but-3-en-2-one, e.g. Ionone beta; Isobutyl isobutyrate; Isobutyl quinolone; Isopropyl methyl-2-butyrate; (2E,6Z)-3,7-dimethylnona-2,6-dienenitrile, e.g. Lemonile; 3,7-dimethylocta-1,6-dien-3-ol, e.g. Linalool; 2,6-dimethylhept-5-enal, e.g. Melonal; Methyl amyl ketone; Methyl benzoate; Methyl heptenone; Methyl Hexyl Ketone; Phenyl ethyl acetate; Tetrahydro myrcenol; Patchouli Oil; Tridecen-2-nitrile; 6-methoxy-2,6-dimethyloctanal, e.g. Calypsone; 5-tert-butyl-2-methyl-5-propyl-2H-furan, e.g. Cassyrane; (4E)-9-hydroxy-5,9-dimethyl-4-decenal, e.g. Mahonial; 1-methyl-2-(5-methylhex-4-en-2-yl) cyclopropyl)methanol, e.g. Rosyfolia; and 3-(4-isobutyl-2-methylphenyl)propanal, e.g. Nympheal.

Preferred fragrance ingredients include, for instance, ambrofix (dodecahydro-3a,6,6,9a-tetramethyl naphtho[2,1-b]furan), radjanol (2-ethyl-4-(2,2,3-trimethyl-cyclopent-3-enyl)-but-2-en-1-ol), benzyl salicylate, cis-3-hexenyl salicylate, coumarin, cyclamen aldehyde, dihydrojasmonate, hedione (methyl dihydrojasmonate), lilial (3-(4-tert-butylphenyl)-2-methylpropanal), nympheal (3-(4-isobutyl-2-methylphenyl)propanal), methyl ionone, phenyl ethyl phenyl acetate, tetrahydrogeranyl acetate, trimofix (reaction products of acetic anhydride and 1,5,10-trimethyl-1,5,9-cyclodecatriene), and tropional (3-(1,3-benzodioxol-5-yl)-2-methylpropanal).

The fragrance component, or any fragrance ingredients forming a part of the fragrance component may be presented in the form of free fragrance oil, or in encapsulated form, or both as free oil and in encapsulate form. Suitable encapsulated media include matrices of water soluble, modified starch.

Starches suitable for encapsulating fragrances are modified starches, which can be made from, raw starch, pregelatinized starch, modified starch derived from tubers, legumes, cereal and grains, for example corn starch, wheat starch, rice starch, waxy corn starch, oat starch, cassava starch, waxy barley, waxy rice starch, sweet rice starch, amioca, potato starch, tapioca starch and mixtures thereof.

Modified starches suitable for use as the encapsulating matrix include starches that are modified chemically, physically, e.g. through heat or pressure, or enzymatically. They include hydrolyzed starch, acid thinned starch, starch esters of long chain hydrocarbons, starch acetates, starch octenyl succinate, and mixtures thereof. Starch esters having a degree of substitution in the range of from about 0.01% to about 10.0% may be used to encapsulate the fragrance ingredients. The hydrocarbon part of the modifying ester should be from a C5 to C16 carbon chain.

The deodorizing composition of the present invention is readily incorporated into all manner of deodorant composition bases, in any product format. In particular, the deodorizing composition is dissolvable or miscible in deodorant composition bases at levels that provide efficacious deodorancy effects. In particular, the deodorizing composition can be incorporated into a deodorant composition base at any level necessary to achieve a desired deodorizing effect.

Consequently, in a further aspect, the present invention also provides a deodorant consumer product comprising the deodorizing composition of the present invention.

Particular deodorant compositions of the invention may contain levels of deodorizing agent such that the finished deodorant consumer product comprises up to about 20 wt % of the at least one zinc carboxylate salt, especially zinc neodecanoate, more particular 2 to 10 wt %, more particularly still about 2 to 5 wt %, e.g. about 4 wt %. Given the fact that the zinc neodecanoate is dissolved in or is miscible with a deodorant composition, it does not leave any unsightly residues when it is applied to a site in need of treatment, or to any other surfaces that come into contact with the treated site.

Particular deodorant compositions of the invention may contain levels of deodorizing agent such that the finished deodorant consumer product comprises up to about 30 wt % of aluminium chlorohydrate, more particular 2 to 20 wt %, more particularly still about 5 to 10 wt %. Typical ranges for sticks and oil gels are from about 15 wt % to about 20 wt % or more, for roll-ons from about 5 wt % to about 15 wt % or more, and for aerosols from about 5 wt % to about 10 wt % or more.

Furthermore, it was found that the deodorant consumer product applied to a surface in need of treatment, for example the human skin, forms a thin film, which is somewhat occlusive and allows a fragrance component to evaporate slowly over time. This results in a substantially linear release of fragrance over a sustained period of time. This surprising finding allows the preparation of deodorant compositions to deliver substantially constant scent impression over a sustained period of time.

The deodorizing compositions of the present invention may be used to eliminate malodours as the form, e.g. in the axilla. Key odorants in axillary sweat include: short chain fatty acids, e.g. 3-hydroxy-3-methyl hexanoic acid (HMHA), 3-methyl-2-hexenoic acid (Schizophrenic acid), or 4-ethyl octanoic acid (Goat acid); sulphanylalcohols (thiols) with low olfactory thresholds, e.g. 3-methyl-3-sulphanylhexan-1-ol (sweat thiol), 2-methyl-3-sulphanylbutan-1-ol (onion thiol), or 3-mercapto-hexan-1-ol; steroids, e.g. 5α-androst-16-en-3-one or 5α-androst-16-en-3α-ol. Other acids are also often present, e.g. butyric acid, isovaleric acid, hexanoic acid, or octanoic acid. In particular, the deodorizing compositions of the present invention can scavenge thiols as they emanate in the axilla.

The deodorizing composition of the present invention can be used in any deodorant consumer product formats known in the art for application to sites containing, or proximate to sites containing, sources of human, animal or environmental malodour. The deodorizing composition is particularly useful in the topical application to the human body, and more particularly still, the human axilla. Suitable product formats include wax-based sticks, soap-based sticks, roll-on suspensions, solutions, emulsions or gels, squeeze-sprays, pump-sprays and aerosols.

In a preferred embodiment, the deodorant consumer product is in the form of an aerosol. The advantageous effect of zinc carboxylate on the suspension of aluminium chlorohydrate in a deodorant base is particularly important for aerosol consumer products.

In addition to deodorizing composition of the present invention, each deodorant consumer product format can contain its own selection of additional components conventionally employed in the particular product format. The types of additional components are well known in the art, and a non-limiting selection of such components is listed herein below.

Deodorant consumer product of the present invention typically include a fragrance component and an emollient system, and may contain any number of optional ingredients that are described below and/or known to the skilled artisan.

The fragrance component may be incorporated into the deodorant consumer product as part of the deodorizing composition, as described herein above, or as a part of the deodorant composition base.

In an alternative embodiment, the deodorizing composition may be in the form of a kit of parts comprising a first part consisting essentially of a solution of at least one zinc carboxylate salt, especially zinc neodecanoate, and the fragrance component, and a second part comprising aluminium chlorohydrate in a suitable solvent. In a further alternative, the fragrance component may be split between said first and second parts. The parts are intended to be incorporated separately, sequentially or simultaneously to a deodorant composition base during the preparation of a deodorant consumer product.

The levels of fragrance component contained in the deodorizing composition should be effective to provide a desired scent impression and/or to provide malodour prevention/suppression or masking.

Generally, the deodorizing composition of the present invention may comprise the total fragrance component at concentrations ranging from about 0.05 wt % to about 10 wt % based on the total amount of the deodorizing composition.

Deodorizing composition and deodorant consumer products of the present invention may contain an emollient composition that may consist of at least one or a combination of different emollient ingredients. The emollients are preferably liquid under ambient conditions, and comprise at least one emollient having a solubility parameter greater than about 9 and more preferably greater than about 11, and a vapour pressure below about 2 mm Hg at 25° C. Depending on the type of product form desired, concentrations of the emollient(s) in the deodorant compositions can range from about 10 wt % to about 90 wt % based on the total weight of the deodorant composition.

Emollients suitable for use in the deodorizing compositions of the present invention include, but are not limited to, topically safe and effective organic, silicone-containing or fluorine-containing, volatile or non-volatile, polar or non-polar, provided that the resulting combinations of emollients form a solution or other homogenous liquid or liquid dispersion at the selected processing temperature of the composition. Processing temperatures for the deodorant compositions can range from about 15° C. to about 150° C. depending on product form. Preferred emollients with the requisite solubility parameter and volatility include but are not limited to: propylene glycol, dipropylene glycol, tripropylene glycol, diethylene glycol, triethylene glycol, PEG-4, PEG-8, 1,2 pentanediol, 1,2 hexanediol, hexylene glycol, and glycerin.

Other emollients can be included in the product to provide other benefits to the deodorant such as, for example, good skin feel or skin moisturization. Other examples of suitable emollients include C2 to C20 monohydric alcohols, C2 to C40 dihydric or polyhydric alcohols, alkyl ethers of polyhydric and monohydric alcohols, volatile silicone emollients such as cyclopentasiloxane, non-volatile silicone emollients such as dimethicone, mineral oils, polydecenes, and petrolatum.

Deodorizing compositions may contain thickening or structuring agents in order to provide a desired hardness and application characteristics to the compositions. The thickening or structuring agent concentrations may range from about 0.1 wt % to about 30 wt %, based on the total weight of the deodorant composition depending on the type of product and thickening or structuring agent. Preferred inclusion ranges for stick products are from about 4 to about 20 wt %.

Depending on the chosen product form, the deodorizing compositions of the present invention may employ a propellant. Suitable propellants include, but are not limited to, dimethylether, 1,1 difluoroethane, 1,1,1,2 tetrafluoro ethane, carbon dioxide, butane, isobutane, propane, isopentane, pentane, nitrous oxide, carbon dioxide, halogenated hydrocarbons such as trichlorofluoromethane, dichlorodifluoromethane, dichlorotetrafluoroethane trichlorotrifluoroethane, trichlorotetrafluoroethane, and monochlorodifluoromethane, and combinations thereof. The total propellant concentration in the deodorizing compositions can range from about 5% to about 99%, more typically from about 15% to about 90%, even more preferably from about 20% to about 70%, by weight of the deodorizing composition.

In addition to the aforementioned components, the deodorizing compositions of the present invention may further comprise one or more components, which may modify the physical or chemical characteristics of the compositions. Non-limiting examples of such components include, but are not limited to, pH buffering agents, additional malodour controlling agents, humectants, soothing agents, dyes and pigments, medicaments, baking soda and related materials, preservatives, and soothing agents such as aloe vera, allantoin, D-panthenol, avocado oil and other vegetative oils, and lichen extract.

Suitable additional deodorant active ingredients may include any topical material that is known or otherwise effective in preventing or eliminating malodour associated with perspiration. Suitable deodorant active ingredients may be selected from the group consisting of antimicrobial agents (e.g., bactericides, fungicides), malodour-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palm-ethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, famesol, and combinations thereof.

The deodorizing compositions of the present invention can be formulated in any of the known or otherwise effective product formats. Representative product formats include solid and solid-like forms (e.g., sticks, waxes, powders), liquids (e.g., aerosol sprays, pump sprays, mist sprays, roll-ons, wipes), and semi-solids (e.g., gels, creams, soft solids, lotions).

Aerosol compositions are a preferred product format according to the invention.

A propellant is a major component of an aerosol composition and the remainder of the deodorant composition may contain any of the ingredients referred to hereinabove, useful or conventionally used in such product formats.

Particularly preferred product formats are at least essentially anhydrous aerosol products.

An at least essentially anhydrous deodorizing composition is a product that contains less than 2 wt %, more particularly less than 0.5 wt % water, and is especially free of water. More particularly, any water that is present in the product is not added during the preparation of the product, but is merely present as a residue that may be contributed by any of the mixed components.

In one embodiment, the deodorizing compositions of the present invention are free or substantially free of thiol compounds.

In one embodiment, the deodorizing compositions of the present invention are free or substantially free of polar oil derivatives, in particular of polar oil derivatives having an Inorganic Organic Balance (I.O.B.) value of 0.1 or more.

In another aspect, the invention is directed to a method of manufacturing a deodorizing composition referred to herein above, said method comprising the step of incorporating the deodorizing agent into a deodorant base, in which the deodorizing agent is soluble or miscible.

For purposes of maintaining or enhancing deodorant efficacy or retaining a pleasant scent impression, it may be beneficial to separate one or more fragrance ingredients and the deodorizing agent to prevent their premature mixing or even to maintain their compatibility. The separation can be effected by maintaining these components in physically separate locations. One or more fragrance ingredients can be encapsulated to maintain separation from zinc neodecanoate and/or aluminium chlorohydrate.

The deodorizing compositions according to the present invention can be prepared by any effective technique, suitable for providing a deodorizing composition of the desired form and having the ingredients described herein. Many such techniques are described in the deodorizing composition arts for the described product forms.

A deodorizing composition in aerosol format is filled into canisters capable of withstanding pressures generated by the composition, employing conventional filling apparatus and conditions. The canister can conventionally be a commercially available metal canister fitted with a dip tube, valve and spray nozzle through which the formulation is dispensed.

Deodorizing compositions are useful for all manner of applications concerned with the treatment of human, animal or environment malodour, including uses in home care, oral care, personal care and fabric care products.

Home care includes air fresheners, dishwashing product, surface cleaners, toilet cleaners, and absorbent products, such as diapers and feminine hygiene products.

Oral care includes tooth pastes and mouthwashes.

Personal care includes hair care, deodorant or antiperspirant deodorant products, bath and shower products and soaps.

Fabric care includes pre-treatment products, detergents and conditioners or softeners.

Deodorizing compositions of the present invention may be applied to a site containing a source of malodour in any known or otherwise effective method. Such methods include the application to a site of a safe and efficacious amount of the deodorizing composition.

The deodorizing compositions of the present invention are particularly useful in the treatment of human body odours by the topical application of the composition to the axilla or other area of the skin in any known or otherwise effective method for controlling malodour associated with perspiration. These methods comprise applying to the axilla or other area of the human skin a safe and effective amount of the deodorizing composition of the present invention.

In a further aspect, the present invention also relates to a method of suspending aluminium chlorohydrate in an at least essentially anhydrous solvent, wherein at least one zinc carboxylate salt is added.

In a further aspect, the present invention also relates to a method of preventing clumping of aluminium chlorohydrate in a deodorizing composition or a deodorant consumer product, wherein the deodorizing composition or deodorant consumer product is provided with at least one zinc carboxylate salt.

In yet a further aspect, the present invention also relates to a method of preventing clogging of a nozzle of a deodorant spray containing a deodorizing composition, said a deodorizing composition comprising aluminium chlorohydrate, wherein the deodorizing composition is provided with at least one zinc carboxylate salt.

In the above three methods, the at least one zinc carboxylate salt is preferably selected from the group consisting of zinc neodecanoate, zinc ricinoleate, and zinc acetate. Particularly preferably, the at least one zinc carboxylate salt is zinc neodecanoate.

In a preferred embodiment, the at least one zinc carboxylate salt is provided in an amount to obtain a concentration of the at least one zinc carboxylate salt in the deodorizing composition or deodorant consumer product of up to about 20 wt %, more particular 2 to 10 wt %, more particularly still about 2 to 5 wt %, e.g. about 4 wt %.

The present invention is further illustrated by means of the following non-limiting examples:

Example 1: Model Alcoholic Aerosol Formulations with Aluminium Chlorohydrate The following model aerosol formulations were prepared in clear glass vials:

|  | Sample 1 | Sample 2 | Sample 3 | Sample 4 |
|---|---|---|---|---|
| 'standard' aluminium chlorohydrate | 5% | 5% | — | — |
| 'activated' aluminium chlorohydrate | — | — | 5% | 5% |
| zinc neodecanoate | 4% | — | — | 4% |
| isopropyl myristate | | | 2% | |
| ethanol | 34% | 38% | | 38% | 34% |
| pentane* | | | 55% | |

*Pentane was used to represent the propellant, and is much easier to handle and store the resulting formulation than the propellants typically used in aerosols.

The glass vials were left at ambient temperature for at least 1 day, then shaken by hand prior to visual inspection. The results are shown in FIG. 1 (samples 1 through 4 being aligned from left to right). As is clearly visible, the aluminium chlorohydrate is only suspended in the samples containing zinc neodecanoate.

Example 2: Underarm Malodour Performance

Aerosols were prepared using the following test formulations:
- 1% fragrance, 4% zinc neodecanoate, 2% Dowanol TPM, 1% Eutanol G, 32% ethanol, 60% propellant
- 1% fragrance, 10% aluminium chlorohydrate, 0.8% disteardimonium hectorite, 12% cyclomethicone, 76.2% propellant (propellant=isobutane/propane mix)

5 days prior to testing, male subjects substituted their normal body wash with an unperfumed product (Sanex 0% Bodywash) and were asked to only use a deodorant supplied (Lynx Attract for Him). On the morning before the test, the male subjects were asked to shower using an unperfumed shower gel provided and not use any antiperspirant product or apply any other fragranced products.

Subjects reported to a panel suite in the morning in two groups for test product application.

The administrator applied 1.0 g of each product to each subject's axilla. Each subject wore both of the test formulations (one on each axilla region). The manner in which each test formulation was applied (left or right axilla) was randomised. Each of a subject's axilla was then coded with a random code number. The subjects were asked not to shower until after the test had been completed the next day. The subjects were also provided with a list of rules, by which they had to abide for the duration of the test. The rules included no swimming and no gym activity between test formulation application and assessment.

The subjects' axillae were thereafter tested by sensory panellists. The members of the sensory panels were selected on a basis of their olfactory sensory acuity and thereafter received training for a period of 4-6 months. Their training enabled them to identify individual odour characteristics and score their perceived intensity against given standards in a consistent manner.

The sensory panellists were asked to rate the perceived malodour intensity for each of the subject's axilla using a 0-100 line scale. The order of samples assessed was predetermined using a balanced randomisation. The axillae were assessed in a sequential monadic way. The panellists were asked to assess directly from the subject's axillae 24 hours after application.

Figure 2:
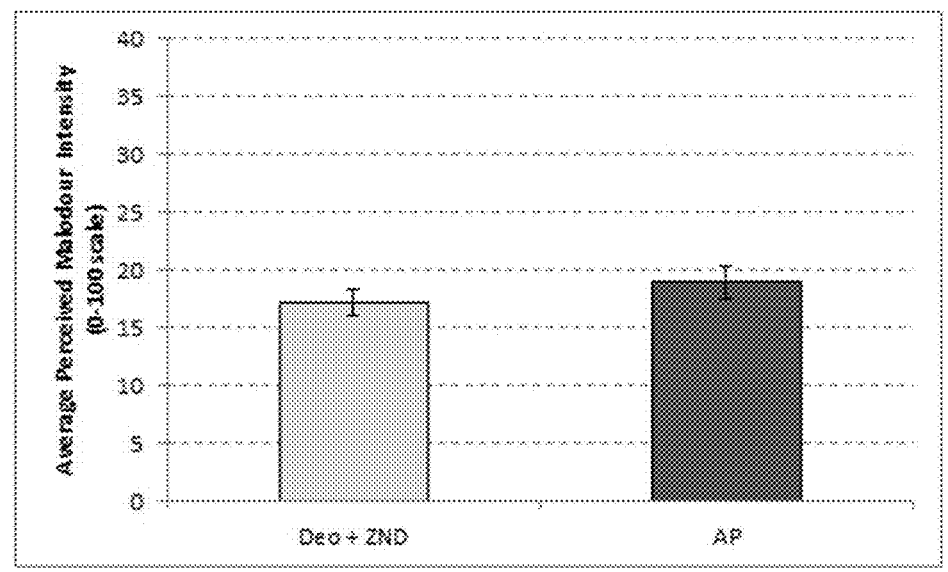
FIG. 2 is a graph of reported malodor perception by panelists rating compositions rating certain test compositions comprising zinc neodecanoate and certain test comopsitoins containing aluminum chlorohydrate.

10 subjects participated in the test. The subjects were separated into two groups to be assessed by the panellists and each group was assessed by 22 panellists. The data was analysed using an analysis of variance and multiple comparison test with the confidence level at 95%. Results are shown graphically in FIG. 2.

It was found that the underarms treated with zinc neodecanoate (Deo+ZND) had equivalent malodour intensity than the underarms treated with aluminium chlorohydrate (AP).

Example 3: Purification of Neodecanoic Acid by Pressure Hydrogenation and Distillation An autoclave vessel (Premex 120 mL) was charged with neodecanoic acid (70.0 g; Umecore) and Rhodium on alumina (1.0 g; Fluka puriss) and was then pressurized with 100 bar hydrogen. The mixture was stirred at 150° C. for 32 h.

After pressure release and venting, the mixture was diluted with MTBE (100 mL) and filtered by suction. The filtrate was concentrated in a rotary evaporator under reduced pressure to yield 56.0 g (80% yield) of a colourless liquid, of which 54.6 g were distilled over a 15 cm Vigreux column at 80-85° C. (p=0.12 mbar, bath temperature 128° C.).

Of the 8 collected fractions, No 3-7 were olfactorily pure and combined to yield 32.3 g (46%) of a clear colourless oil. The material still had an intrinsic odour of its own, but lacked the sulfury/rubbery/phenolic off-notes unpurified neodecanoic acid typically has.

Example 4: Purification of Neodecanoic Acid by Distillation

Neodecanoic acid (152.3 g; Umecore) was distilled over a 15 cm Vigreux column at 89-90° C. (p=0.02 mbar, bath temperature 140-156° C.).

Of the 14 collected fractions, No 8-14 were olfactorily pure and combined to yield 85.5 g (56%) clear colourless oil. Olfactory quality seemed similar to that of example 3.

The invention claimed is:

1. A deodorizing composition comprising a suspension which includes zinc neodecanoate and aluminium chlorohydrate.

2. The deodorizing composition according to claim 1, wherein the zinc neodecanoate is present in a concentration of from about 1% by weight to about 20% by weight.

3. The deodorizing composition according to claim 1, wherein the zinc neodecanoate and the aluminium chlorohydrate are present in a respective weight ratio of from about 1.5:1 to about 1:10.

4. The deodorizing composition according to claim 1, which further comprises an at least essentially anhydrous solvent.

5. The deodorizing composition according to claim 1, further comprising at least one fragrance ingredient.

6. The deodorizing composition according to claim 5, wherein the at least one fragrance ingredient is selected from the group consisting of: 3,7-dimethyloct-6-enal; 3,7-dimethyloct-6-en-1-ol; 2,4-dimethylcyclohex-3-enecarbaldehyde; (E)-dec-4-enal; ethyl 2-methyl butyrate; 1- phenylethyl acetate; (Z)-hex-3-en-1-yl acetate; hexyl acetate; isoamyl acetate; *Litsea cubeba* oil; Nonanal; Orange oil; Orange terpenes; prenyl acetate; 4- methyl-2-(2-methylprop-1-en-1-yl)tetrahydro-2H-pyran; 4-methylene-2-phenyltetrahydro-2H-pyran; 2,4-dimethylcyclohex-3-enecarbaldehyde; 2,6,10- trimethylundec-9-enal; Armoise oil Morocco; 8-(sec-butyl)-5,6,7,8- tetrahydroquinoline; (2E)-3-phenylprop-2-enal; (E)-3,7-dimethylocta-2,6-dienal; ethyl caproate; 1,3,3-trimethyl-2-oxabicyclo[2.2.2]octane; *Eucalyptus;* 1-(1,2,8,8-tetramethyl-1,2,3,4,5,6,7,8-octahydronaphthalen-2-yl) ethanone; hexyl isobutyrate; (E)-4-(2,6,6-trimethylcyclohex-1-en-1-yl)but-3-en-2-one; isobutyl isobutyrate; isobutyl quinolone; isopropyl methyl-2-butyrate; (2E,6Z)-3,7-dimethylnona-2,6- dienenitrile; 3,7-dimethylocta-1,6-dien-3-ol; 2,6-dimethylhept-5-enal; methyl amyl ketone; methyl benzoate; methyl heptenone; methyl hexyl ketone; phenyl ethyl acetate; tetrahydro myrcenol; Patchouli Oil; tridecen-2-nitrile; 6-methoxy2,6-dimethyloctanal; 5-tert-butyl-2-methyl-5-propyl-2H-furan; (4E)-9-hydroxy5,9-dimethyl-4-decenal; 1-methyl-2-(5-methylhex-4-en-2- yl)cyclopropyl)methanol; 3-(4-isobutyl-2-methylphenyl)propanal; and mixtures thereof.

7. A deodorant consumer product comprising the deodorizing composition according to claim 1.

8. The deodorant consumer product according to claim 7 in the form of an aerosol.

9. A method of suspending aluminium chlorohydrate in an at least essentially anhydrous solvent, wherein the method includes the step of: adding zinc neodecanoate to the said solvent and the aluminium chlorohydrate.

10. A method of reducing or preventing clumping of aluminium chlorohydrate in a deodorizing composition or in a deodorant consumer product, the method comprising the step of: including zinc neodecanoate in the deodorizing composition or the deodorant consumer product.

11. A method of reducing or preventing clogging of a nozzle of a deodorant spray containing a deodorizing composition comprising aluminium chlorohydrate, the method comprising the step of: including zinc neodecanoate in said deodorizing composition.

12. The method according to claim 9, wherein the zinc neodecanoate provided in the suspension in an amount to obtain a concentration of the zinc neodecanoate in a deodorizing composition or a deodorant consumer product of up to about 20 wt %.

13. The deodorizing composition according to claim 5, further comprising at least 5 fragrance ingredients.

14. The deodorizing composition according to claim 13, further comprising at least 10 fragrance ingredients.

15. The method according to claim 12, wherein the zinc neodecanoate in the suspension is provided in an amount to obtain a concentration of the zinc neodecanoate in the deodorizing composition or in the deodorant consumer product of 2 to 10 wt %.

16. The method according to claim 15, wherein the zinc neodecanoate in the suspension is provided in an amount to obtain a concentration of the zinc neodecanoate in the deodorizing composition or in the deodorant consumer product of 2 to 5 wt %.

17. The deodorizing composition according to claim 3, wherein the zinc neodecanoate and the aluminium chlorohydrate are present in a respective weight ratio of from about 2:1 to about 1:5.

18. The deodorizing composition according to claim 17, wherein the zinc neodecanoate and the aluminium chlorohydrate are present in a respective weight ratio of from about 1:1 to about 1:2.

19. The method according to claim 10, wherein the zinc neodecanoate is provided in an amount to obtain a concentration of the zinc neodecanoate in the deodorizing composition or the deodorant consumer product of up to about 20 wt %.

20. The method according to claim 19, wherein the zinc neodecanoate is provided in an amount to obtain a concentration of the zinc neodecanoate in the deodorizing composition or the deodorant consumer product of 2 to 10 wt %.

21. The method according to claim 20, wherein zinc neodecanoate is provided in an amount to obtain a concentration of the zinc neodecanoate in the deodorizing composition or the deodorant consumer product of 2 to 5 wt %.

22. The method according to claim 11, wherein the zinc neodecanoate is provided in an amount to obtain a concentration of the zinc neodecanoate in the deodorizing composition of up to about 20 wt %.

23. The method according to claim 22, wherein the zinc neodecanoate is provided in an amount to obtain a concentration of the zinc neodecanoate in the deodorizing composition of 2 to 10 wt %.

24. The method according to claim 23, wherein zinc neodecanoate is provided in an amount to obtain a concentration of the zinc neodecanoate in the deodorizing composition of 2 to 5 wt %.

\* \* \* \* \*